(12) United States Patent
Purifoy et al.

(10) Patent No.: US 6,178,970 B1
(45) Date of Patent: Jan. 30, 2001

(54) FOOT SANDER

(76) Inventors: Veena E. Purifoy, 508 Boynton Ave., Berkley, CA (US) 94707; Christy A. Beville, 1930 7th Ave., Apt. 103, Oakland, CA (US) 94606

(*) Notice: Under 35 U.S.C. 154(b), the term of this patent shall be extended for 0 days.

(21) Appl. No.: 09/340,687

(22) Filed: Jun. 29, 1999

Related U.S. Application Data

(60) Provisional application No. 60/191,472, filed on Mar. 23, 2000.

(51) Int. Cl.[7] .............................. A45D 29/18; A45D 29/05
(52) U.S. Cl. ...................... 132/76.4; 132/75.8; 132/75.3; 132/73.5
(58) Field of Search .................... 132/76.4, 75.8, 132/75.6, 75.3, 73.5, 73

(56) References Cited

U.S. PATENT DOCUMENTS

| D. 286,852 | 11/1986 | Ditmanson | D8/71 |
|---|---|---|---|
| D. 364,226 | 11/1995 | Hartman | D24/147 |
| 1,373,970 | * 4/1921 | Peasley | 132/76.4 |
| 1,869,197 | * 7/1932 | Holz | 132/75.8 |
| 2,746,461 | * 5/1956 | Bocchino | 132/76.4 |
| 3,131,701 | 5/1964 | Emerson . | |
| 3,176,695 | * 4/1965 | Mueller | 132/75.8 |
| 3,797,505 | * 3/1974 | Gilhaus et al. | 132/76.4 |
| 4,213,471 | 7/1980 | Burian et al. | 132/73.6 |
| 4,408,623 | 10/1983 | Murray | 132/73.6 |
| 4,440,182 | * 4/1984 | Holm | 132/75.8 |
| 4,541,443 | * 9/1985 | Brothers et al. | 132/75.6 |
| 4,643,207 | * 2/1987 | Grahame | 132/76.4 |
| 5,033,485 | * 7/1991 | Hauerwas et al. | 132/75.6 |
| 5,187,827 | 2/1993 | Wei | 15/22.1 |
| 5,465,740 | * 11/1995 | Kim | 132/76.4 |
| 5,520,618 | 5/1996 | Massiet | 601/136 |
| 5,759,093 | * 6/1998 | Rodriguez | 132/75.6 |
| 5,819,757 | * 10/1998 | Baekkelund | 132/75.6 |

FOREIGN PATENT DOCUMENTS

| 143137 | 11/1983 | (EP) . |
|---|---|---|
| 417177 | 9/1934 | (GB) . |

* cited by examiner

Primary Examiner—John J. Wilson
Assistant Examiner—Robyn Kieu Doan
(74) Attorney, Agent, or Firm—Richard C. Litman

(57) ABSTRACT

A portable personal grooming appliance for removing calluse and rough skin from the feet by sanding. The appliance includes body having a rechargeable battery powered motor encased therein An orbital motion head and supporting disc, adapted to be driven b, the motor, is positioned on a first end of the body. A sheet of sandpaper or a massaging pad is adapted to be removably attached to the orbital motion disc for foot sanding or massaging when applied thereto. The appliance body is orthopedically engineered to fit the palm of a user to enhance gripping. A travel case is provided to facilitate portability.

4 Claims, 2 Drawing Sheets

FOOT SANDER

CROSS-REFERENCE TO RELATED APPLICATION

This application claims the benefit of U.S. Provisional Patent Application Ser. No. 60/191,472, filed Mar. 23, 2000.

BACKGROUND OF THE INVENTION

1. Field of the Invention

The present invention relates generally to personal grooming devices. More specifically, the present invention is directed to a portable, rechargeable, personal sander or massager adapted to remove calluses and other aberrant cellular growth from the feet.

2. Description of the Related Art

There are many known prior art devices for removing corns an calluses from the feet of a user. Exemplification of such devices is shown in U.S. Pat. Nos. Des. 364,226 (Hartmann), 3,131,701 (Emerson), and 5,520,618 (Massiet). It is noted, however, that the cited devices require manual manipulation.

U.S. Pat. Nos. 4,213,471 (Burian et al.), 4,408,623 (Murray), and Int'l Patent Number 143,137 disclose battery operates personal grooming appliances but none contemplate the use of such appliances for foot sanding or massaging.

U.S. Pat. Nos. Des. 286,852 (Ditmanson) and 5,187,827 (Wei) respectively disclose a motorized cue tip shaper and a motorized cleaning implement. Patent Number 417,177 (Great Britain) is drawn to a method of making sandpaper. None of the instant patents is concerned with personal foot grooming.

None of the above inventions and patents, taken either single or in combination, is seen to describe a personal, rechargeable, battery operated foot sanding or massaging device as will subsequently be described and claimed in the present invention.

SUMMARY OF THE INVENTION

The present invention comprises a portable, rechargeable battery operated, motorized, personal grooming appliance wherein orbital motion head is adapted to support a replaceable sandpaper sheet or massage pad. The appliance is primarily adapted to be used for removal of calluses, corns, and rough skin from the feet. It is obvious, however, that the appliance can be used on other problem skin areas as desired. A travel case is provided to store the appliance, extra sheets (and grades) of sandpaper, and massage pads.

Accordingly, it is a principal object of the invention to provide a motorized personal grooming appliance adapted to sand or massage a user's feet.

It is another object of the invention to provide a portable personal grooming appliance adapted to sand or massage a user's feet.

It is a further object of the invention to provide a personal grooming appliance for sanding or massaging a user's feet, which appliance utilizes replaceable sandpaper sheets or massage pads.

Still another object of the invention is to provide a travel case for a personal grooming appliance, which appliance is adapter to sand or massage a user's feet.

It is an object of the invention to provide improved elements and arrangements thereof in an apparatus for the purposes described which is inexpensive, dependable and fully effective it accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
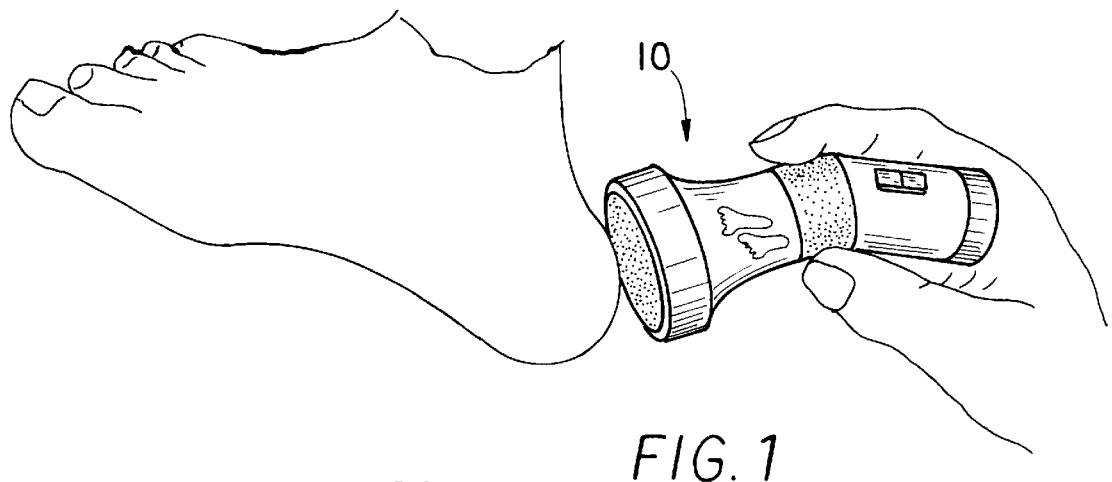
FIG. 1 is an environmental, perspective view of a foot sander or massager according to the present invention.
Figure 2:
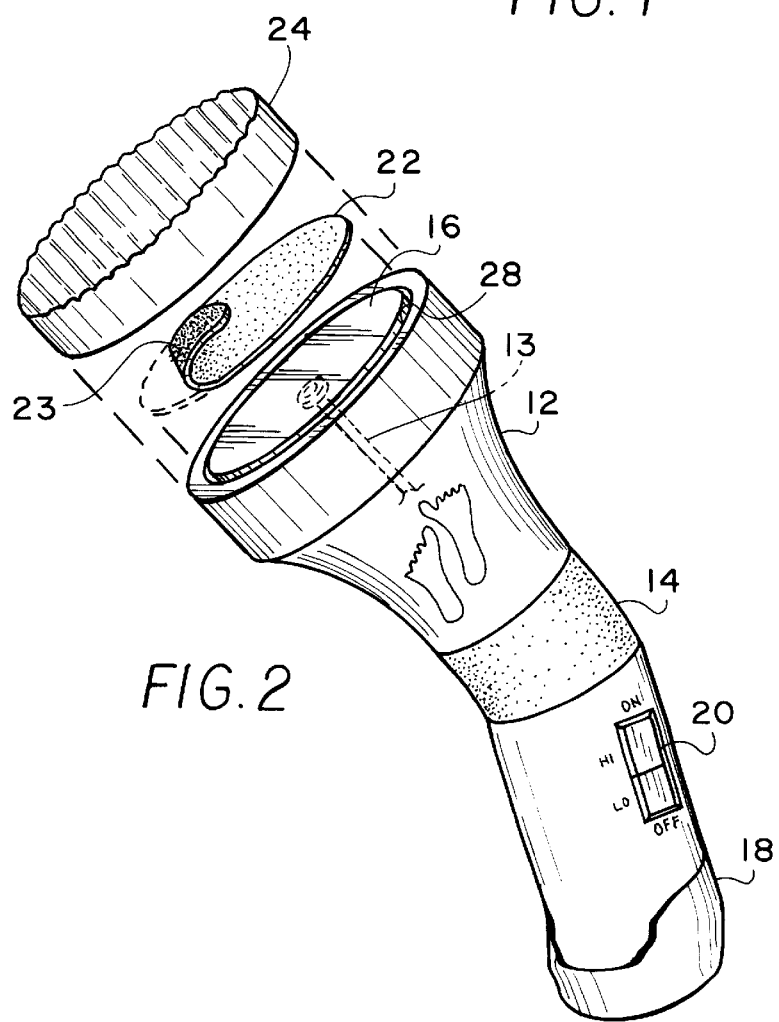
FIG. 2 is a partially exploded perspective view of a foot sander or massager according to the present invention.

FIGS. 1 and 2 depict a portable motorized personal grooming appliance at 10. Appliance 10 comprises a plastic or metal hollow body member 12 which is orthopedically engineered to fit the shape of a user's hand for improved gripping. As best seen in FIG. 2, a rubberized surface is provided at 14 to further enhance gripping. A orbital motion head 16 is disposed at a first end of body member 12 and is mounted for rotation on a shaft 13. The head 16 includes a flat surface or plastic supporting disc for receiving an adhesive backed sandpaper sheet or massaging pad 22. Shaft 13 is driven by a rechargeable battery operated motor (not shown) which motor and battery are encased in hollow body 12. The motor and rechargeable battery are conventional and are not part of the inventive concept; however, it in order to obtain a smoothing effect on the skin surface, the motor chosen is adapted to cause the head 16 to be moved in an orbital sanding motion. Such orbital motion requires that the head 16 be provided with enough clearance relative to the body 12 to prevent interference, as represented by space 28.

Rechargeable batteries to operate the motor can be inserted at a second end of body 12 opposite to the first end. A removable cap 18 closes the second end of body 12. Alternatively, the appliance can be provided with a plug-in recharging system as well known in the art. An on-off, two speed switch 20 is positioned on body 12 for controlling the operation of the encased motor. Sandpaper or massaging sheet 22 is removably attached to orbital motion head 16. Sheet 22 may utilize any effective adhesive 23 for removable attachment to orbital motion head 16. A cover member 24 is removably disposed on the first end of body 12 to afford protection for the orbital motion head when the appliance is not in use.

Figure 3:
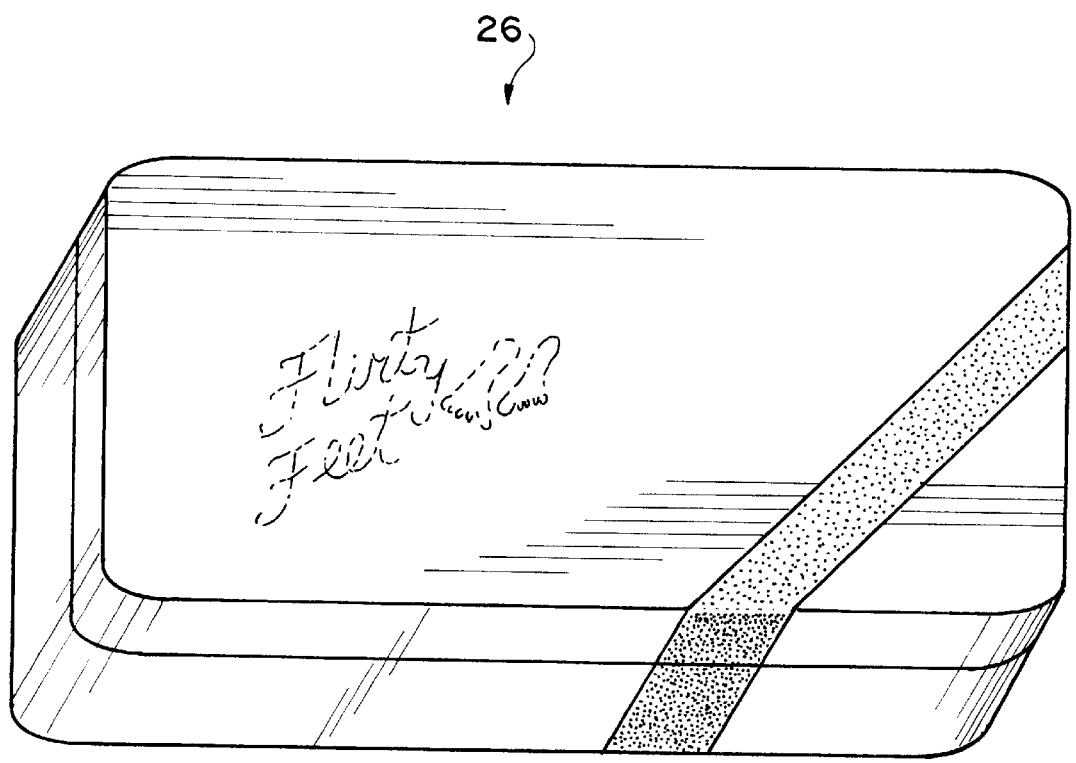
FIG. 3 is a perspective view of a travel case for a foot sander or massager according to the present invention.

FIG. 3 illustrates a travel case 26 utilized to store and transport the appliance 10 and extra sandpaper or massaging sheets so as to facilitate portability. Each sandpaper or massaging sheet may include a plurality of precut and adhesive discs, squares, or other shapes which are sized to cover head 16, and which may be peeled from a release liner (not shown) when needed. Travel case 26 may be made of any durable material (rayon, nylon, plastic, etc.) and may be provided with suitable fastening means (zipper, VELCRO, snaps, etc.). A kit may be provided wherein a plurality of sheets, the case, and the appliance are packaged together. Appliance 10 and travel case 26 may be made in a variety of colors (vivid or pastel) to sate the aesthetic appetites of potential users.

It is to be understood that the present invention is not limited to the sole embodiment described above, but encompasses any and all embodiments within the scope of the following claims.

We claim:

1. A personal grooming appliance comprising:

a hollow body, said hollow body having a first end and an open second end;

an orbital motion head disposed on said first end of said hollow body;

means for treating calluses and other aberrant cellular growth on the feet;

said means including a sheet mounted upon said orbital motion head, said sheet having a rear surface with means for removably attaching the sheet to the head, said means for removably attaching being an adhesive disposed on said rear surface, whereby said sheet can be easily attached and removed from said orbital motion head;

a cap member closing said open second end of said hollow body;

a cover member removably positioned on said first end of said hollow body; and a two-speed switch disposed on said hollow body wherein said switch is operative to control a motor for rotating said orbital motion head.

2. A personal grooming device as defined in claim 1 wherein said hollow body is orthopedically engineered to fit the shape of a user's palm.

3. A personal grooming device as defined in claim 2 wherein said sheet is a sandpaper sheet.

4. A personal grooming device as defined in claim 2 wherein said sheet is a massaging pad.

* * * * *